United States Patent
Weigel et al.

(10) Patent No.: US 7,485,748 B2
(45) Date of Patent: Feb. 3, 2009

(54) PROCESS FOR THE PRODUCTION OF 2-HYDROXY-4-METHYTHIOBUTYRIC ACID AMMONIUM SALT

(75) Inventors: Horst Weigel, Rodenbach (DE); Christoph Weckbecker, Gründau-Lieblos (DE); Klaus Huthmacher, Gelnhausen (DE)

(73) Assignee: Degussa AG, Dusseldorf (DE)

( * ) Notice: Subject to any disclaimer, the term of this patent is extended or adjusted under 35 U.S.C. 154(b) by 0 days.

(21) Appl. No.: 10/547,280

(22) PCT Filed: Mar. 26, 2004

(86) PCT No.: PCT/EP2004/003208

§ 371 (c)(1),
(2), (4) Date: Aug. 30, 2005

(87) PCT Pub. No.: WO2004/089863

PCT Pub. Date: Oct. 21, 2004

(65) Prior Publication Data

US 2006/0178529 A1 Aug. 10, 2006

(30) Foreign Application Priority Data

Apr. 9, 2003 (DE) ............................... 103 16 110

(51) Int. Cl.
*C07C 315/00* (2006.01)
(52) U.S. Cl. .................................................. 562/581
(58) Field of Classification Search .................. 562/581
See application file for complete search history.

(56) References Cited

U.S. PATENT DOCUMENTS

| | | | | |
|---|---|---|---|---|
| 2,745,745 A | | 5/1956 | Blake et al. | |
| 4,085,193 A | * | 4/1978 | Nakajima et al. | 423/239.1 |
| 4,374,753 A | * | 2/1983 | Pullukat et al. | 502/111 |
| 4,482,643 A | * | 11/1984 | Harju et al. | 502/242 |
| 5,330,953 A | * | 7/1994 | Meina | 502/208 |
| 5,672,745 A | * | 9/1997 | Hasseberg et al. | 562/559 |

FOREIGN PATENT DOCUMENTS

| | | |
|---|---|---|
| EP | 0 143 100 A2 | 5/1985 |
| EP | 0 433 611 A1 | 6/1991 |
| JP | 03-093753 | 4/1991 |
| JP | 03-093754 | 4/1991 |
| JP | 10-128113 | 5/1998 |
| WO | WO 96/09403 | 3/1996 |
| WO | 01/60789 A1 * | 8/2001 |
| WO | WO 01/60789 A1 | 8/2001 |
| WO | WO 02/00869 A2 | 1/2002 |
| WO | WO 02/070717 A2 | 9/2002 |

* cited by examiner

Primary Examiner—Kamal A Saeed
Assistant Examiner—Robert Havlin
(74) Attorney, Agent, or Firm—Smith, Gambrell & Russell, LLP

(57) ABSTRACT

A process for preparing 2-hydroxy-4-methylthiobutyric acid ammonium salt involves reacting 3-methylthiopropionaldehyde with hydrogen cyanide to form 2-hydroxy-4-methylthiobutyronitrile, and subsequently hydrolyzing the 2-hydroxy-4-methylthiobutyronitrile by catalytic hydrolysis to form the ammonium salt of the 2-hydroxy-4-methylthiobutyric acid in a single process step. One catalyst may be used in the hydrolysis for the whole reaction. The catalyst is preferably a solid containing a titanium compound such as, e.g., titanium nitride, titanium sulfide or titanium dioxide. The 2-hydroxy-4-methylthiobutyric acid ammonium salt produced by this process is nutritional and can be used as an additive in feedstuffs.

14 Claims, No Drawings

PROCESS FOR THE PRODUCTION OF 2-HYDROXY-4-METHYTHIOBUTYRIC ACID AMMONIUM SALT

REFERENCE TO RELATED APPLICATIONS

This application claims the benefit of German priority application 103 16 110.4 of Apr. 9, 2003 and PCT/EP2004/003208 of Mar. 26, 2004.

FIELD OF THE INVENTION

The invention relates to a process for the production of 2-hydroxy-4-methylthiobutyric acid ammonium salt, as well as to the use of the 2-hydroxy-4-methylthiobutyric acid ammonium salt produced by this process. In particular, the invention relates to an alternative process for the hydrolysis of 2-hydroxy-4-methylthiobutyronitile.

BACKGROUND OF THE INVENTION

Nutrition-enhancing feed additives are an essential component of animal nutrition today. They are used to improve the utilization of the nutrient supply, stimulate growth and promote protein formation. One of the most important of these additives is the essential amino acid methionine, which occupies a prominent position as a feed additive particularly in poultry rearing. In this field, however, so-called methionine substitutes or methionine hydroxy analogue, (abbreviated to MHA) are gaining increasing importance, since they exhibit growth-stimulating properties similar to those of the amino acid known for this purpose.

The racemic form of 2-hydroxy-4-methylthiobutyric acid is a methionine substitute that has been known for a long time, which is used mainly in animal nutrition, particularly in the rearing of poultry, as a feed additive. This MHA is used instead of methionine and improves the utilization of protein in the feed. In addition, in the form of its calcium salt, it is also used pharmaceutically in the treatment of renal insufficiency.

The industrial production of the above-mentioned MHA typically takes place by reaction of 3-methylthio-propionaldehyde with hydrogen cyanide to form 2-hydroxy-4-methylthiobutyronitrile (MMP cyanohydrin), which is then hydrolyzed in two steps to form MHA. A two-step hydrolysis of the nitrile with stoichiometric quantities of strong mineral acids, such as sulfuric acid, via the step of the carboxamide, to form MHA and the ammonium salt of the mineral acid is described in numerous patents (e.g. EP 0 143 100). In complex extractions with organic solvents and backwash of the MHA into an aqueous phase, the product is separated from the mineral acid, which is used in excess, and its ammonium salt. Inorganic waste products form in considerable quantities in this process.

As an alternative to the acid hydrolysis, enzymatic processes have been described. In WO 96/09403, a nitrilase is described which can hydrolyze the two enantiomers of MMP cyanohydrin to form racemic MHA ammonium salt. However, the enzymes are obtainable only with difficulty and their recovery from the reaction solution is very complex. The problem of recovering the enzyme is solved in WO 02/00869 by the use of water-insoluble, enzyme-containing granules. However, the production of the enzyme-containing granules is difficult, and the half-life of the enzyme activity is given in ranges of up to 70 hours. A significantly longer-lasting activity is expected of a catalyst in an economic process.

In another synthesis strategy, the nitrile is hydrolyzed to the amide in a first step and then the amide is further hydrolyzed to the ammonium salt of MHA. WO 02/070717 discloses a nitrile hydratase, which specifically saponifies MMP cyanohydrin to MHA amide. The hydrolysis of cyanohydrin with the aid of a heterogeneous catalyst is also known. The production of the corresponding acid amide from acetone cyanohydrin with manganese dioxide and an oxidizing agent is disclosed in the patent EP 0 433 611. In the Japanese published patent application Hei 10-128113 from 1998, the production of a catalytically active manganese oxide is claimed, which catalyses the reaction of MMP cyanohydrin to the amide with very high selectivity. However, it is also possible to isolate the amide in a sulfuric acid hydrolysis of the cyanohydrin. WO 01/60789 shows that the methionine amide and its hydroxy analogue can be hydrolyzed with titanium-containing catalysts to form the ammonium salt of methionine or MHA. Here, however, there is the disadvantage of a two-step reaction with two different catalysts and an isolation of the intermediate.

The main commercial form of MHA is a highly concentrated aqueous solution. During storage, an equilibrium forms from the monomeric compound with the di-, tri- and oligomeric MHA. Its effectiveness as a feed additive, compared with methionine, is further reduced by the proportion of the higher molecular weight compounds. It is known that salts of MHA in solid and dissolved form are stable and no higher molecular weight compounds form.

OBJECT OF THE INVENTION

In view of the prior art discussed here, the object of the present invention is to find a technically simple, economic process for the production of a form of MHA with high nutritional value, which avoids, or at least markedly reduces, the above-mentioned disadvantages associated with the production and also with the use of known methionine hydroxy analogues.

Despite the intensive work on improving the process for the production of MHA, no alkaline hydrolysis of the nitrile group of MMP cyanohydrin is known because, under the necessary hydrolysis conditions, a back reaction to the aldehyde and to hydrogen cyanide preferentially takes place. The present invention concerns a catalytic hydrolysis of cyanohydrin to form the ammonium salt of MHA, wherein no inorganic salt is formed as waste and only one catalyst is used for the entire reaction.

SUMMARY OF THE INVENTION

It has been found that the hydrolysis of 2-hydroxy-4-methylthiobutyronitrile can be performed with suitable catalysts in such a way that the reaction to form the 2-hydroxy-4-methylthiobutyric acid ammonium salt surprisingly takes place in one process step.

DETAILED DESCRIPTION OF THE INVENTION

Suitable catalysts are titanium-containing solids, of which titanium compounds such as titanium nitride or titanium sulfide, but especially titanium dioxides ($TiO_2$), are particularly suitable. $TiO_2$ is known in various crystal modifications, of which anatase is the more catalytically active form. The catalytic activity is further improved if some of the oxide functions are present as hydroxide. Anatase can be used in pure form, but also in a mixture with rutile or other metal compounds, such as oxides of manganese, molybdenum, niobium, vanadium or tungsten or zeolites or mixtures of two or more of these compounds.

The catalyst can be used as a powder, extrudate or in a pressed form, together with a support material such as for example aluminium oxide or zirconium oxide. The form of the catalyst is of only minor significance for its effectiveness and is adapted to the requirements of the plant design.

It is known that MMP cyanohydrin is immiscible with water at ambient temperature. However, its solubility in water increases markedly with a rise in temperature, thus a saturated aqueous solution at 57° C. already contains approx. 25% MMP cyanohydrin.

The hydrolysis reaction in the presence of a suitable titanium-containing catalyst is performed at a temperature of between 60° C. and 190° C., preferably at 70° C. to 150° C. To this end, it is necessary that, at temperatures above the boiling point of the solution, the reaction is performed in a pressure-proof reaction vessel. The pressure itself has no effect on the reaction but is necessary at a reaction temperature above the boiling point of the solution and corresponds to the vapor pressure of the liquid.

Two moles of water react with one mole of cyanohydrin to form the MHA ammonium salt. It is advantageous to use water, in excess. The proportion of cyanohydrin in the mixture with water may be in the range of 1 to 60 wt. %, preferably 3 to 40 wt. %.

The hydrolysis, catalyzed with titanium compounds, may be performed both continuously and batchwise. Thus, for example, the cyanohydrin may be pumped into a hot suspension of the catalyst with water or a preheated solution of the two reactants is passed through a heated fixed bed with the catalyst. Other technical solutions are possible.

The quantity of catalyst used is dependent on its activity and the reaction conditions selected (temperature, quantity of water); and on the way in which the reaction is conducted. To achieve short reaction times, it is advantageous to select the largest possible quantity of catalyst. Thus, for example, a powdered catalyst with a surface area of 300 $m^2$/g can be employed in a quantity of 0.1 to more than 2 g per g of cyanohydrin. When an extrudate with a specific surface of 45 $m^2$/g is used, the quantity of catalyst required is 0.3 to 5 g per g of cyanohydrin. The quantity of catalyst is not critical, but primarily influences the reaction time required. The catalyst can be used several times.

On completion of the reaction, the solid catalyst is separated from the reaction solution by known processes and can be reused, and the solution is concentrated up to the desired concentration, optionally after clarifying with activated carbon, or is converted to the MHA calcium salt with calcium hydroxide.

A small amount of methionine may be formed during hydrolysis, depending upon how the reaction is conducted. This does not have to be separated off, since it has the same area of application in animal nutrition.

Another aspect of the present invention is the use of the MHA ammonium salt produced according to the invention instead of D,L-methionine as an additive in feedstuffs, and a feed additive containing the MHA ammonium salt produced according to the invention.

The following examples are intended to illustrate the subject-matter of the invention without having a limiting effect. The MMP cyanohydrin employed was produced from industrial MMP with a water content of 1.6% by a known process by reaction with hydrogen cyanide, and then stabilized with phosphoric acid. A content determination using HPLC gave 96.5%.

EXAMPLE 1

In a pressure vessel with a free volume of 250 ml, equipped with a stirrer, a metal basket containing 23.8 g of an extruded titanium dioxide (d=4 mm), Aerolyst 7708®, which is commercially available from Degussa AG, was anchored. The catalyst consisted of a mixture of anatase and rutile. After adding 7.5 g of MMP cyanohydrin (96.5%) and 143 g of water, the reactor was sealed and heated to 120° C., with stirring. After 3 hours, the solution no longer contained any cyanohydrin, but 5.7 wt. % MHA ammonium salt and 0.2% MHA amide.

EXAMPLE 2

The pressure vessel used in example 1 was filled with 22 g of an extruded titanium dioxide (d=1 mm), Aerolyst 7710® from Degussa AG, 15 g of MMP cyanohydrin and 135 g of water. After stirring for five hours at 130° C., the temperature was reduced to 100° C. and the reaction solution was removed through a dip pipe. 10 g of MMP cyanohydrin-and 90 g of water were then fed in and heated to 130° C. with stirring. After 5.5 hours, the solution no longer contained any cyanohydrin, but 11.1 wt. % MHA ammonium salt, 0.8 wt. % methionine and 0.1 wt. % MHA amide.

EXAMPLE 3

15 g of MMP cyanohydrin, 135 g of water and 24 g of titanium dioxide were boiled under reflux in a glass vessel with a stirrer and reflux condenser. The titanium dioxide used, FINNTi S140 from Kemira, is in powder form and has a surface of 250 to 350 $m^2$/g. After 4.5 hours, cooling was carried out and the catalyst was filtered off. The reaction solution contained 11.2 wt. % MHA ammonium salt, 0.3 wt. % methionine, 0.4 wt-% MHA amide and no cyanohydrin.

What is claimed is:

1. A process for the production of 2-hydroxy-4-(methylthio)butyric acid ammonium salt comprising reacting of 3-(methylthio)propionaldehyde with hydrogen cyanide to form 2-hydroxy-4-methylthiobutyronitrile and subsequently hydrolyzing said nitrile by catalytic hydrolysis to the ammonium salt of the 2-hydroxy-4-(methylthio)butyric acid in a single process step, with one catalyst employed in the whole hydrolysis reaction, wherein the catalyst is a solid titanium compound.

2. The process according to claim 1, wherein the titanium compound is titanium nitride, titanium sulfide or titanium dioxide.

3. The process according to claim 2, wherein the titanium dioxide contains the crystal modification of anatase.

4. The process according to claim 1, wherein the catalyst is an oxidic titanium compound, in which some of the oxide functions are present as hydroxide.

5. The process according to claim 1, wherein a pure form of anatase or a mixture of anatase with rutile or other metal compounds is the catalyst.

6. The process according to claim 5, wherein said mixture contains an oxide of manganese, molybdenum, niobium, vanadium or tungsten or zeolites or mixtures of two or more of these compounds.

7. The process according to claim 1, wherein, on completion of the reaction, the catalyst is separated from the reaction solution and reused.

8. The process according to claim 1, wherein the catalyst is used in a continuous process.

9. A process for the production of hydroxy 2-hydroxy-4-(methylthio)butyric acid amide by catalytic hydrolysis of 2-hydroxy-4-methylthiobutyronitrile, wherein the catalyst is a titanium-containing solid and contains a titanium compound.

10. A process for the production of a composition having at least 5.7% by weight of 2-hydroxy-4-(methylthio)butyric acid ammonium salt which comprises reacting of 3-(methylthio)propionaldehyde with hydrogen cyanide to form 2-hydroxy-4-methylthiobutyronitrile and subsequently hydrolyzing said nitrile by catalytic hydrolysis to the ammonium salt of the 2-hydroxy-4-(methylthio)butyric acid in a single process step, with one catalyst employed in the whole hydrolysis reaction, wherein the catalyst is a solid titanium compound.

11. The process of claim 10, wherein the composition does not contain cyanohydrin.

12. The process of claim 10, wherein composition comprises 0.8% by weight of methionine.

13. The process of claim 10, wherein the composition comprises 0.1 to 0.4% by weight of 2-hydroxy-4-(methylthio)butyric acid amide.

14. A process for the production of a composition having 2-hydroxy-4-(methylthio)butyric acid ammonium salt and methionine which comprises reacting of 3-(methylthio)propionaldehyde with hydrogen cyanide to form 2-hydroxy-4-methylthiobutyronitrile and subsequently hydrolyzing said nitrile by catalytic hydrolysis to the ammonium salt of the 2-hydroxy-4-(methylthio)butyric acid in a single process step, with one catalyst employed in the whole hydrolysis reaction, wherein the catalyst is a solid titanium compound and the ratio of 2-hydroxy-4-(methylthio)butyric acid ammonium salt to methionine by weight is about 11:0.8 to 11.2:0.3.

* * * * *